United States Patent
Hughes et al.

(10) Patent No.: US 10,350,130 B2
(45) Date of Patent: Jul. 16, 2019

(54) UNIVERSAL TENSEGRITY JOINTS FOR HUMAN EXOSKELETON

(71) Applicant: EKSO BIONICS, INC., Richmond, CA (US)

(72) Inventors: Mike Hughes, Oakland, CA (US); Russdon Angold, American Canyon, CA (US); Jeff Vickers, Richmond, CA (US); Bradley Roan, Vacaville, CA (US); Kurt Amundson, Berkeley, CA (US); Nicholas Fleming, Oakland, CA (US)

(73) Assignee: Ekso Bionics, Inc., Richmond, CA (US)

( * ) Notice: Subject to any disclaimer, the term of this patent is extended or adjusted under 35 U.S.C. 154(b) by 164 days.

(21) Appl. No.: 15/329,529

(22) PCT Filed: Jul. 15, 2016

(86) PCT No.: PCT/US2016/042418
§ 371 (c)(1),
(2) Date: Jan. 26, 2017

(87) PCT Pub. No.: WO2017/015086
PCT Pub. Date: Jan. 26, 2017

(65) Prior Publication Data
US 2017/0209330 A1    Jul. 27, 2017

Related U.S. Application Data

(60) Provisional application No. 62/193,919, filed on Jul. 17, 2015.

(51) Int. Cl.
*A61H 3/00* (2006.01)
*A61F 2/66* (2006.01)
(Continued)

(52) U.S. Cl.
CPC ............... *A61H 3/00* (2013.01); *A61F 2/604* (2013.01); *A61F 2/605* (2013.01); *A61F 2/66* (2013.01);
(Continued)

(58) Field of Classification Search
CPC ........ A61H 1/0237; A61H 1/0262; A61F 3/00
(Continued)

(56) References Cited

U.S. PATENT DOCUMENTS 5,020,790 A    6/1991    Beard et al.
5,167,612 A *  12/1992   Bonutti ................. A61F 5/0123
                                                    601/33
(Continued)

FOREIGN PATENT DOCUMENTS

CN    101132753      2/2008
WO    2015/095211    6/2015

*Primary Examiner* — Brian E Pellegrino
(74) *Attorney, Agent, or Firm* — Diederiks & Whitelaw, PLC.

(57) ABSTRACT

An exoskeleton includes first and second compression members configured to be coupled to a wearer of the exoskeleton. A tensegrity joint connects the first compression member to the second compression member, the joint including a tensile member having a first end and a second end. The first end is coupled to the first compression member on a first side of the joint, and the second end is coupled to the first compression member on a second side of the joint opposite the first side.

19 Claims, 10 Drawing Sheets

(51) Int. Cl.
    *A61H 1/02*     (2006.01)
    *A61F 2/60*     (2006.01)
    *B25J 9/00*     (2006.01)
    *B25J 17/00*     (2006.01)
    *A61F 2/50*     (2006.01)

(52) U.S. Cl.
    CPC .......... *A61H 1/0266* (2013.01); *B25J 9/0006* (2013.01); *B25J 17/00* (2013.01); *A61F 2002/5038* (2013.01); *A61H 1/0255* (2013.01); *A61H 2201/0165* (2013.01); *A61H 2201/0192* (2013.01); *A61H 2201/165* (2013.01); *A61H 2201/169* (2013.01); *A61H 2201/1621* (2013.01); *A61H 2201/1642* (2013.01); *A61H 2205/08* (2013.01); *A61H 2205/10* (2013.01); *A61H 2205/12* (2013.01)

(58) Field of Classification Search
    USPC .......... 248/332; 623/48; 602/40, 23, 24, 25, 602/27, 28, 29; 601/33, 34; 128/882
    See application file for complete search history.

(56) References Cited

U.S. PATENT DOCUMENTS

| | | |
|---|---|---|
| 6,824,569 B2 | 11/2004 | Okediji |
| 6,969,365 B2 | 11/2005 | Scorvo |
| 7,192,410 B1 | 3/2007 | Rodgers |
| 7,549,969 B2 | 6/2009 | van den Bogert |
| 8,376,974 B2 | 2/2013 | Nace |
| 8,845,566 B2 | 9/2014 | Johnson et al. |
| 8,894,592 B2 | 11/2014 | Amundson et al. |
| 9,198,821 B2 | 12/2015 | Unluhisarcikli et al. |
| 2005/0216097 A1 | 9/2005 | Rifkin |
| 2007/0004570 A1 | 1/2007 | Afanasenko et al. |
| 2012/0271207 A1 | 10/2012 | Schoen et al. |
| 2013/0245524 A1 | 9/2013 | Schofield |
| 2014/0090677 A1 | 4/2014 | Butler |
| 2014/0276265 A1 | 9/2014 | Caires et al. |
| 2014/0276308 A1 | 9/2014 | Diangelo et al. |
| 2014/0303536 A1 | 10/2014 | Guldalian |
| 2015/0150705 A1 | 6/2015 | Capra et al. |
| 2016/0229049 A1 | 8/2016 | Angold et al. |

\* cited by examiner

UNIVERSAL TENSEGRITY JOINTS FOR HUMAN EXOSKELETON

CROSS REFERENCE TO RELATED APPLICATIONS

This application represents a National Stage application of PCT/US2016/042418, filed Jul. 15, 2016, which claims the benefit of U.S. Provisional Application No. 62/193,919, which was filed on Jul. 17, 2015 and titled "Universal Tensile Joints for Human Exoskeleton". The entire content of these application are incorporated herein by reference.

GOVERNMENT LICENSE RIGHTS

This invention was made with government support under Contract H92222-15-C-0025 awarded by the United States Special Operations Command. The government has certain rights in the invention.

FIELD OF THE OF THE INVENTION

The present invention relates to a device and method that augments a user's carrying capacity and strength, increasing performance and aiding in the prevention of injury during the execution of certain load-bearing or strength-requiring tasks. More particularly, the present invention relates to a device suitable for use by a person engaging in heavy tool use or weight-bearing tasks, the device comprising a set of artificial limbs and related control systems that potentiate improved function of the user's appendages including, but not limited to, greater strength and endurance in the user's legs, allowing for more weight to be carried by the user while walking.

BACKGROUND OF THE INVENTION

Wearable exoskeletons have been designed for medical, commercial and military applications. Medical exoskeletons are designed to help restore a user's mobility. Commercial and military exoskeletons help prevent injury and augment a user's stamina and strength by alleviating loads supported by workers or soldiers during strenuous activities. Exoskeletons designed for use by able-bodied users often act to improve the user's stamina by transferring the weight of a tool or load through the exoskeleton structure and to the ground, thus decreasing the weight borne by the user. For the exoskeleton to transfer this weight to the ground, each exoskeleton support member and exoskeleton joint between the exoskeleton weight and the ground must be able to act as a conduit of this force around the user. This requires a degree of rigidity, seen in the joints of current exoskeletons, that can limit the range of motion of some exoskeleton joints. By limiting the flexibility at these joints, the mobility and maneuverability of the exoskeleton is reduced, thereby limiting the usefulness of the exoskeleton in certain applications. This is an issue in both passive weight-bearing exoskeletons and powered exoskeletons. In the case of powered exoskeletons, the weight of actuators and power systems such as batteries must also be borne by the structure and joints of the exoskeleton.

Current exoskeleton designs rely on inflexible compression members to support the weight of the exoskeleton structure, with the exoskeleton joints being comprised of rotating or pivoting components that connect two rigid members at a fixed distance (the distance being the joint itself) and bear weight through compression. This greatly limits the degrees of freedom of one rigid exoskeleton member relative to the adjoining exoskeleton member. While some exoskeleton joints, such as the knee, require rotation only in a single plane with a fixed distance between the connected rigid members, other joints, such as the hip and ankle, are better served by rotation in two or more planes as well as translation. As one example of the consequences of the limited range of motion of exoskeleton joints, current exoskeleton ankles are incapable of any significant eversion or inversion motion. As a result, the bottom of an exoskeleton foot cannot compensate for a slope in the coronal plane, making current exoskeletons incapable of walking on many types of terrain. As another example, the inability (or reduced ability) of exoskeleton ankle and hip joints to rotate in the transverse plane makes turning a walking or standing exoskeleton difficult. With respect to the hip joint specifically, while the human hip is a ball and socket joint that does not require translation, an exoskeleton hip joint must pass around the human hip. As an exoskeleton hip cannot be collocated with the center of human hip joint rotation, translation about an exoskeleton hip joint allows for greatly improved flexibility for the exoskeleton wearer at the hip—particularly in movements such as medial and lateral rotation or combinations of rotation with adduction, abduction, extension, or flexion. Such improved flexibility would be a great advantage to exoskeletons being worn in highly dynamic environments, such as those seen in athletic activities or combat scenarios.

Due to the limitations imposed on exoskeleton use by the restricted range of motion in exoskeleton joints, there exists a need in the art to develop a device that allows improved flexibility in weight-bearing exoskeleton joints. There also exists a need in the art to develop such a device that is low weight.

SUMMARY OF THE INVENTION

Disclosed herein are devices and methods that allow for greatly improved flexibility in weight-bearing exoskeleton joints. In addition to enhancing the flexibility of exoskeleton joints and allowing for improved exoskeleton mobility under a range of movements and terrain conditions, these devices and methods have additional benefits relating to decreased exoskeleton weight and improved exoskeleton fitting to an exoskeleton user.

In particular, the present invention is directed to an exoskeleton including first and second compression members configured to be coupled to a wearer of the exoskeleton. A tensegrity joint connects the first compression member to the second compression member, the joint including a tensile member having a first end and a second end. The first end is coupled to the first compression member on a first side of the joint, and the second end is coupled to the first compression member on a second side of the joint opposite the first side. Preferably, the joint further includes a tensile member guide through which the tensile member passes.

In one embodiment, each of the first and second ends is directly coupled to the first compression member. In another embodiment, the first end is directly coupled to a first support, the second end is directly coupled to a second support and each of the first and second supports is directly coupled to the first compression member.

The joint further includes a first pulley on the first side of the joint and a second pulley on the second side of the joint. Each of the first and second pulleys is connected to the second compression member. In one embodiment, each of the first and second pulleys is directly coupled to the second compression member. In another embodiment, the first pulley is directly coupled to a first support, the second pulley is directly coupled to a second support and each of the first and second supports is directly coupled to the second compression member.

In one embodiment, the joint is an ankle joint, and one of the first and second compression members is a lower leg support. The other of the first and second compression members is a boot support. In another embodiment, the joint is an abdominal joint, and one of the first and second compression members is a torso support. The other of the first and second compression members is a waist support. In a further embodiment, the joint is a hip joint, and one of the first and second compression members is a waist support. The other of the first and second compression members is an upper leg support.

In one embodiment, the joint constitutes a first tensegrity joint. The exoskeleton further includes a third compression member configured to be coupled to the wearer and a second tensegrity joint connecting the second compression member to the third compression member. The second tensegrity joint includes a tensile member having a first end and a second end. The first end is coupled to the second compression member on a first side of the second tensegrity joint, and the second end is coupled to the second compression member on a second side of the second tensegrity joint opposite the first side.

Additional objects, features and advantages of the invention will become more readily apparent from the following detailed description of preferred embodiments thereof when taken in conjunction with the drawings wherein like reference numerals refer to common parts in the several views.

DESCRIPTION OF THE INVENTION

Detailed embodiments of the present invention are disclosed herein. However, it is to be understood that the disclosed embodiments are merely exemplary of the invention that may be embodied in various and alternative forms. The figures are not necessarily to scale, and some features may be exaggerated or minimized to show details of particular components. Therefore, specific structural and functional details disclosed herein are not to be interpreted as limiting, but merely as a representative basis for teaching one skilled in the art to employ the present invention.

In connection with the present invention, the flexibility of exoskeleton joints is improved by the incorporation of one or more tensile members into an exoskeleton joint. These tensile members act either in tandem with or instead of rotational components of exoskeleton joints to allow a greater degree of freedom and flexibility in the affected joint without compromising the ability of the affected joint to bear weight. Such tensegrity joints are also described in U.S. application Ser. No. 15/023,773, which is incorporated herein by reference.

Unlike the design of current exoskeletons, the human skeletal system is comprised of both inflexible compression members (i.e., bones) as well as tensile members (i.e., ligaments and tendons). These tensile members allow a large range of motion at certain joints by enabling small shifts in the positions of compression members relative to each other. This is well demonstrated by the movements of the bones in the human forearm as the wrist is rotated. While the anatomical design of human joints cannot be directly applied to exoskeleton joints, the principle of tensegrity can be applied to exoskeleton joints. A tensegrity design makes use of compression members that are under continuous compression, with these compression members connected (and held in compression) by tensile members that are under continuous tension. Through use of these tensile members in an exoskeleton joint, the number of degrees of freedom within which two joint-connected compression members can move is increased. Specifically, these tensile-linked joints allow linked compression members to shift relative to each other in additional ways compared to the compression member linkages of current exoskeleton joints (current exoskeleton joints being limited to rotational movements between linked compression members). The increased flexibility at these joints not only improves exoskeleton maneuverability under conditions in which exoskeletons are currently used, such as movement upon flat surfaces, but also allows for exoskeleton use in conditions that preclude the use of current exoskeleton designs, such as terrain sloped steeply in the coronal plane.

In addition to improved joint flexibility, the incorporation of tensile members into exoskeletons also has additional advantages. Tensile members in some cases are substantially lighter than their rigid counterparts, as seen in the components of suspension bridges compared to those of steel frame bridges. In the case of exoskeleton joints, tensile components can replace heavier and more expensive machined joint components. Further, the length of a tensile component can be changed relatively easily (either during manufacture or in post-manufacture adjustment), allowing for improved fitting of an exoskeleton to a user without the more complicated or costly modification of rigid components.

Although a tensile member can be incorporated into an exoskeleton joint such that the tensile member acts similarly to a tensile member found in a physiological joint, this need not be the case. In the present invention, the tensile member actually functions dissimilarly to what is seen in physiological joints. Specifically, concepts were developed to improve the flexibility of exoskeleton joints through the incorporation of a tensile member into the exoskeleton joint in such a way that the tensile member spans both sides of the exoskeleton joint, with the tensile member serving to suspend the exoskeleton structure above the joint from the exoskeleton structure below the joint. The tensile member acts, either alone or in tandem with pulleys or other tensile member guidance components, to allow rotational and translational freedom and flexibility in the affected exoskeleton joint without compromising the ability of the joint to bear weight. The connectivity of the tensile member in the joint is such that the tensile member can slide from one side of the joint to the other, effectively allowing for the length of the tensile member on each side of the joint to change while the total length of the tensile member remains the same, the result being improved joint flexibility without compromise to the weight bearing capacity of the joint. Concepts were further developed to incorporate this joint design into various exoskeleton joints. Based on these concepts, different exoskeleton joints were constructed to validate and demonstrate the feasibility and utility of these concepts in which a tensile member is used in an exoskeleton joint.

Figure 1A:
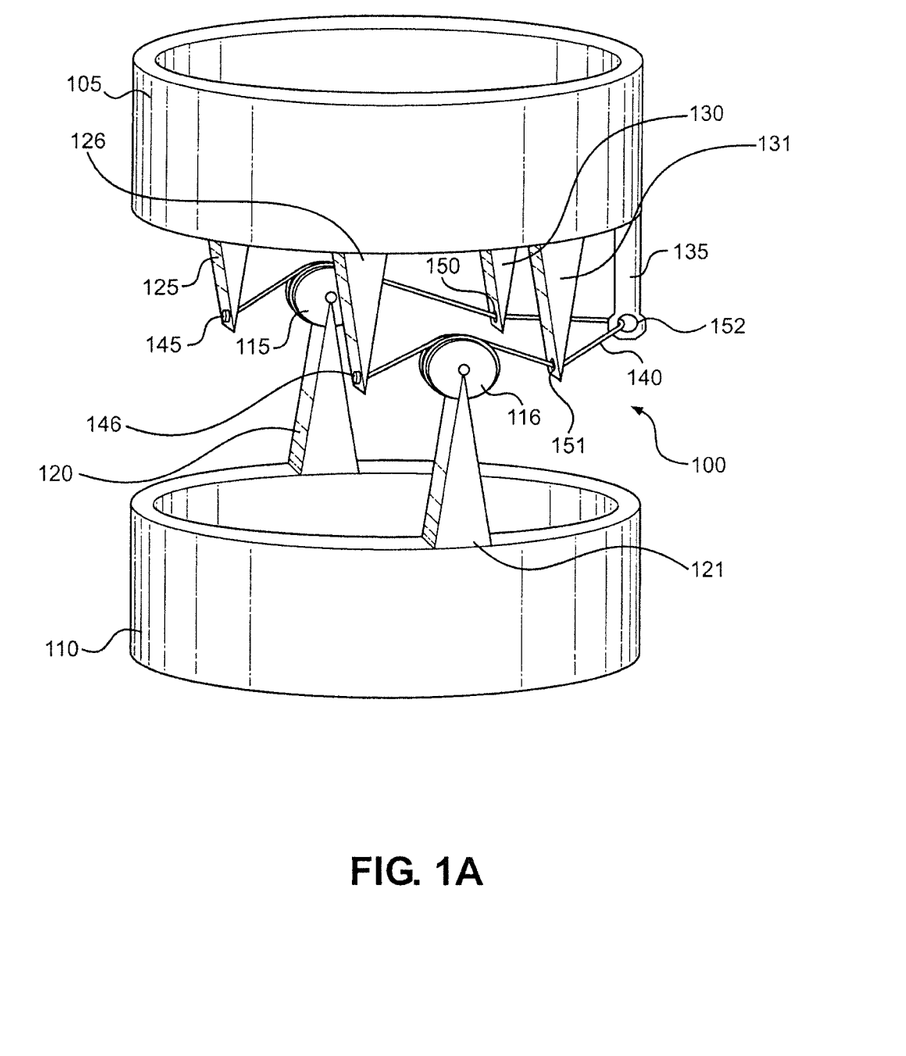
FIG. 1A is a perspective view of a simplified exoskeleton joint constructed in accordance with a first embodiment of the present invention.

With reference now to FIG. 1A, a first embodiment of the present invention is shown. In particular, a simplified exoskeleton joint is labeled 100. Joint 100 connects an upper compression member 105 to a lower compression member 110, with upper compression member 105 being supported over lower compression member 110. Joint 100 includes a right pulley 115 connected to lower compression member 110 by a right support 120 and a left pulley 116 connected to lower compression member 110 by a left support 121. Right support 120 and left support 121 are directly coupled to lower compression member 110. Similarly, a right front support 125, a left front support 126, a right rear support 130, a left rear support 131 and rear guide 135 are directly coupled to upper compression member 105. Joint 100 also includes a tensile member 140 that is directly coupled to right front support 125 and left front support 125 at a right attachment 145 and a left attachment 146, respectively. Tensile member 140 is wrapped around right pulley 115 and left pulley 116 and passes through right rear support 130, left rear support 131 and rear guide 135. As a result of this arrangement, weight is transferred from upper compression member 105 to tensile member 140 by right front support 125, left front support 126, right rear support 130, left rear support 131 and rear guide 135, with this weight then being transferred from tensile member 140 to lower compression member 110 through right pulley 115, left pulley 116, right support 120 and left support 121. Thus, weight is transferred across joint 100 from upper compression member 105 to lower compression member 110. In addition, since tensile member 140 is wrapped around rotatable right and left pulleys 115 and 116 and can slide through guide holes 150-152 provided in right rear support 130, left rear support 131 and rear guide 135, joint 100 can tilt along any axis and/or rotate.

Although joint 100 is not shown as corresponding to any particular exoskeleton joint, it should be understood that joint 100 can be placed around a portion of the human body (e.g., a limb) such that this portion is located inside upper compression member 105 and lower compression member 110. The resulting exoskeletal structure is stiff under compression but is still able to provide three degrees of freedom of rotation collocated with the rotation of the portion of the human body located inside compression members 105 and 110. The manner in which this mechanism can be placed around the human body will become more apparent in connection with the additional embodiments of the present invention discussed below.

Figure 1B:
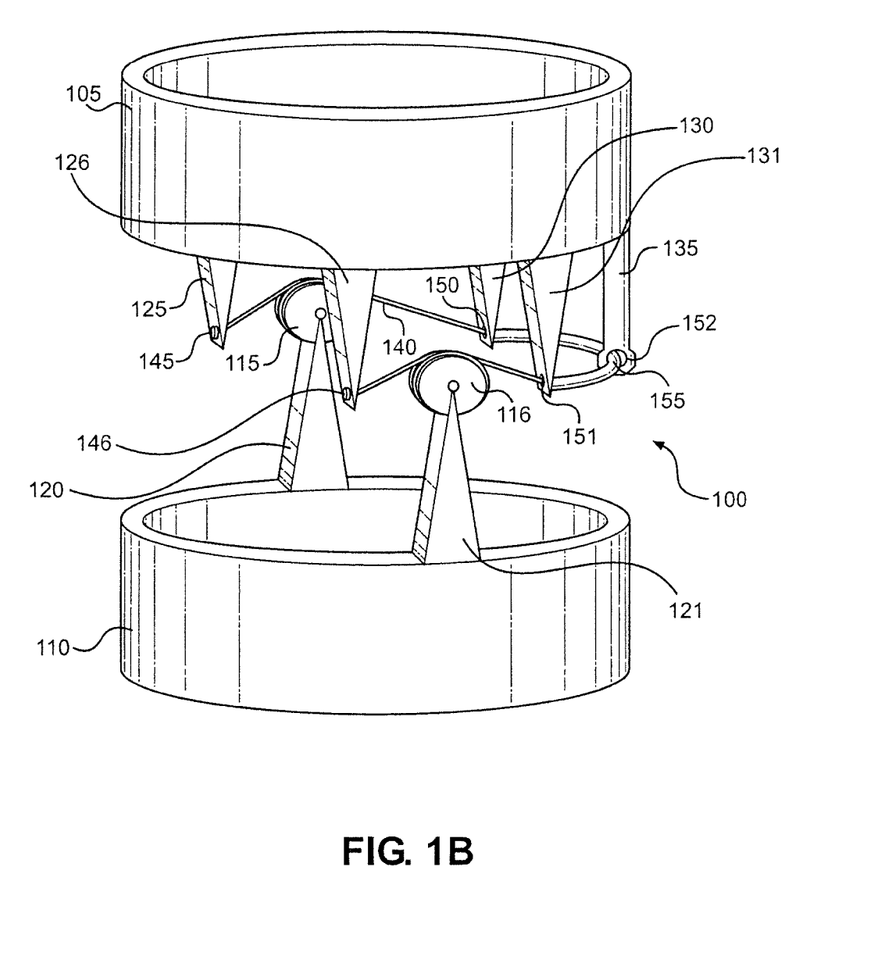
FIG. 1B is a perspective view of the exoskeleton joint of the first embodiment including an additional tensile member guide.

Turning to FIG. 1B, a variation of the exoskeleton joint of the first embodiment is shown. Specifically, a tensile member guide 155 has been added. Tensile member guide 155 guides tensile member 140 through right rear support 130, left rear support 131 and rear guide 135 in such a way as to reduce the chance of tensile member 140 becoming tangled, reduce the wear on tensile member 140 and increase the space bounded by joint 100 (through which a limb or some other portion of an exoskeleton wearer can pass).

Figure 1C:
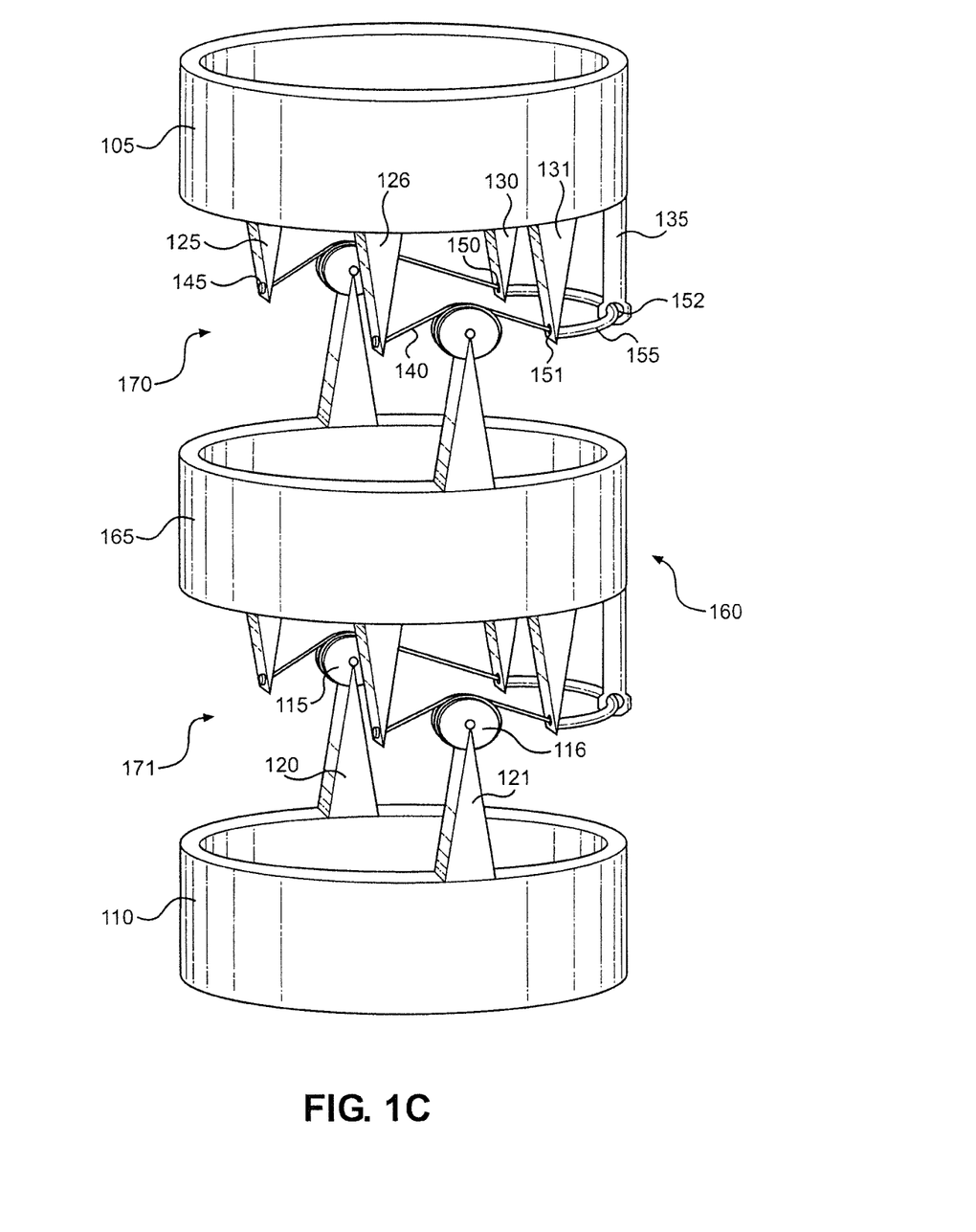
FIG. 1C is a perspective view of the exoskeleton joint of the first embodiment with more than one joint link.

FIG. 1C shows two linked joints constructed in accordance with the first embodiment. In addition to upper compression member 105 and lower compression member 110, a linked joint structure 160 includes an intermediate compression member 165. Intermediate compression member 165 is connected to upper compression member 105 and lower compression member 110 through upper joint 170 and lower joint 171, respectively. Both upper joint 170 and lower joint 171 are able to tilt and rotate in such a way as to improve the flexibility of linked joint structure 160 relative to a single joint structure of the same type (e.g., joint 100). Although FIG. 1C shows two joints 170, 171 linking three compression members 105, 110, 165, it should be recognized that additional joints and compression members can be added if desired.

Figure 1D:
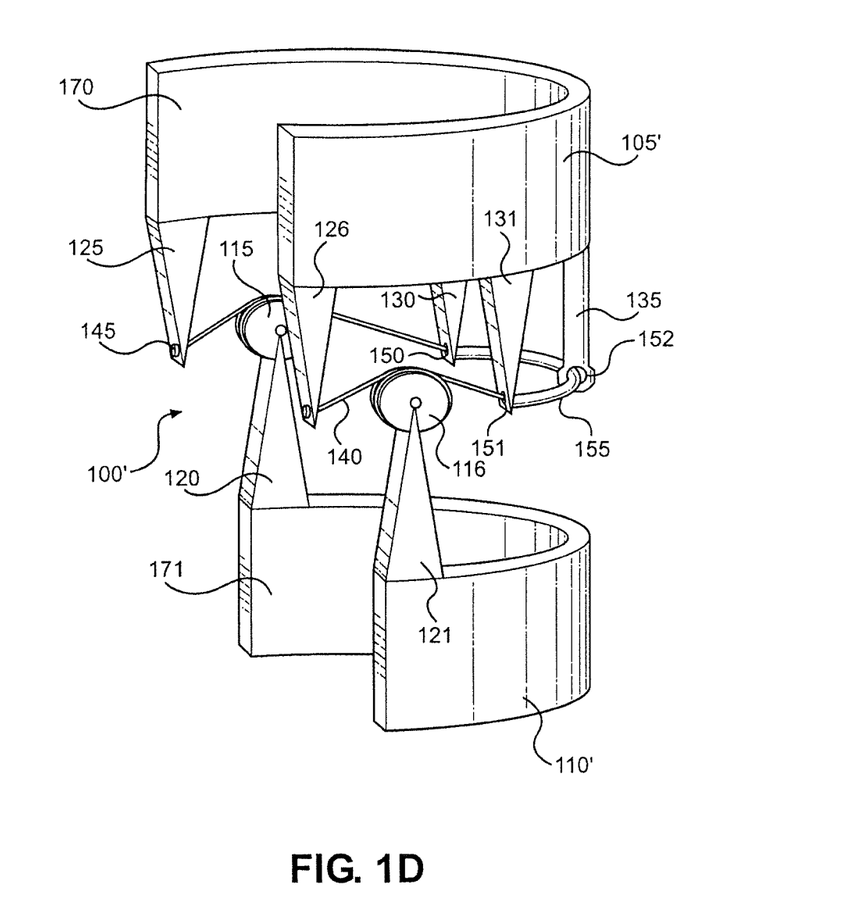
FIG. 1D is a perspective view of the exoskeleton joint of the first embodiment with a portion of the device cut away so as to allow the device to be coupled to a person.

In FIG. 1D, another variation of the exoskeleton joint of the first embodiment is shown. In particular, portions of an upper compression member 105' and a lower compression member 110' have been removed on each side of a joint 100' so as to allow compression members 105' and 110' to be placed around and then coupled to a portion of a person. In other words, upper compression member 105' and lower compression member 110' include openings 175 and 176 through which a portion of a person can be inserted.

Although several variations of the first embodiment have been illustrated, it should be recognized that other changes can be made. For example, the components coupled to upper compression member 105 can be swapped with the components coupled to lower compression member 110 (i.e., pulleys 115 and 116 can be connected to upper compression member 105 while supports 125, 126, 130 and 131 and guide 135 are directly coupled to lower compression member 110). Also, in some arrangements, tensile member 140 winds around each pulley 115, 116 more than one time. In some arrangements, there is more than one pulley on each side. In some arrangements, additional components are present to guide tensile member 140 onto or off of pulleys 115 and 116. Furthermore, in some arrangements, tensile member 140 is a cable. In other arrangements, tensile member 140 is a high strength cord made of a material such as aramid fiber. In some arrangements, tensile member 140 is inelastic. In other arrangements, tensile member 140, or sections thereof, has some elasticity.

The exoskeleton joint of the first embodiment represents a generic or universal joint. Of course, the concepts embodied by this joint can be applied to specific exoskeleton joints that would benefit from improved flexibility (or reduced joint weight) relative to current joint designs. Non-limiting examples of such joints are described below.

Figure 2A:
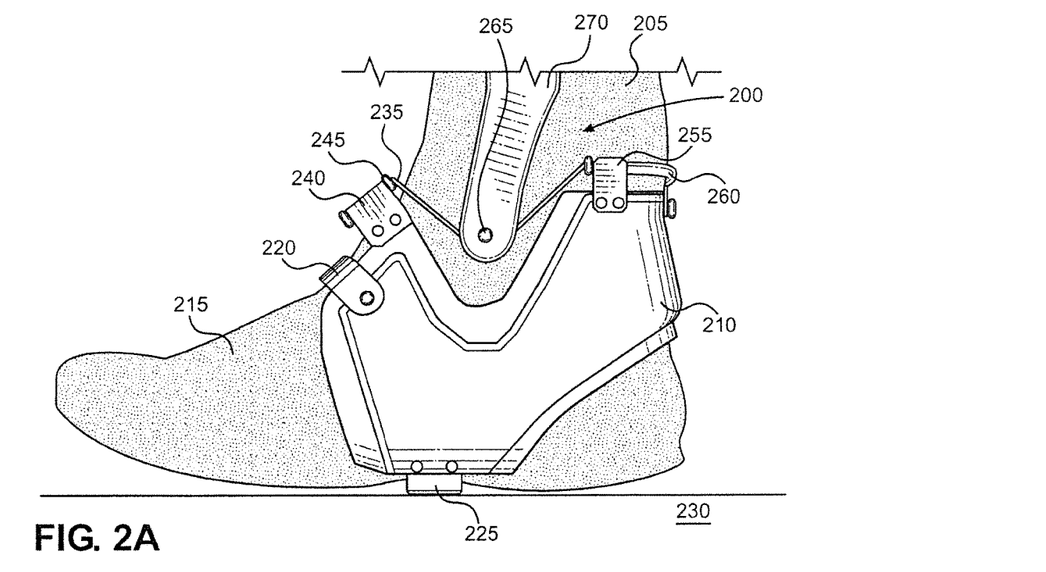
FIG. 2A is a side view of an exoskeleton ankle joint constructed in accordance with a second embodiment of the present invention.
Figure 2B:
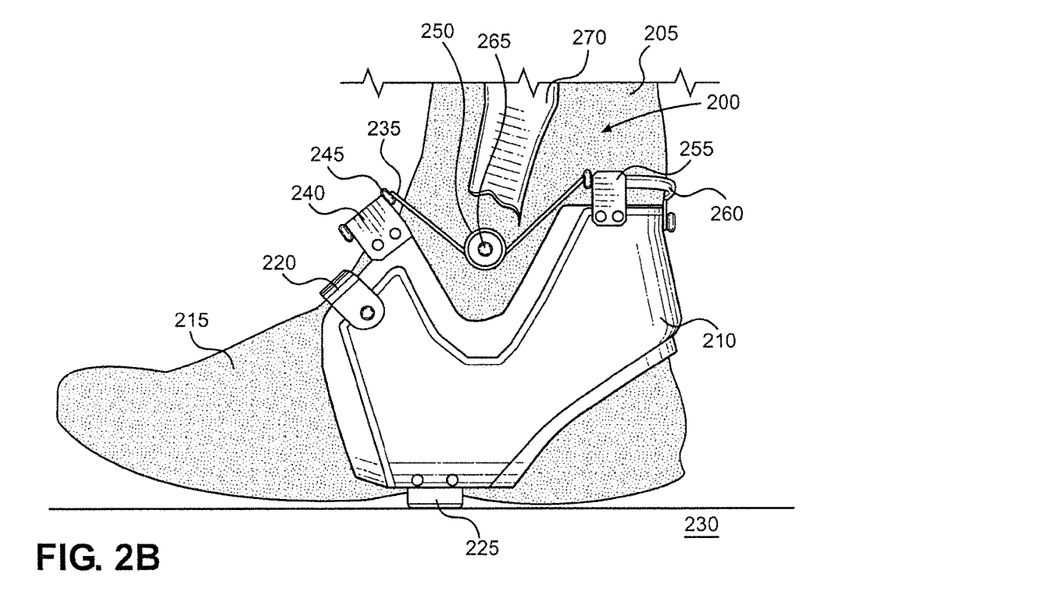
FIG. 2B is a side view of the exoskeleton ankle joint of the second embodiment with a portion of the ankle joint removed to show a pulley on the interior of a lower leg support.

FIGS. 2A-H show an exoskeleton ankle joint 200 constructed in accordance with a second embodiment of the present invention. With initial reference to FIGS. 2A and 2B, joint 200 is shown in connection with a right foot of an exoskeleton wearer (or user) 205. Specifically, a rigid boot support 210 is directly coupled to a boot 215 worn by wearer 205. A strap 220 selectively couples boot support 210 to boot 215 while also limiting ankle roll for the wearer's right foot. Both boot 215 and a ground interaction structure 225 directly coupled to boot support 210 are in contact with a support surface 230 on which wearer 205 is standing. A tensile member 235 is directly coupled to a left front support 240 at a left attachment point 245. Tensile member 235 is wrapped around a left pulley 250 and passes through a left rear support 255 into a tensile member guide 260. Left pulley 250 rotates about a bearing 265, which connects left pulley 250 to a left lower leg support 270. In FIG. 2B, a portion of left lower leg support 270 has been removed such that left pulley 250 can be seen more clearly. Although not shown, left lower leg support 270 is typically coupled to a lower leg of wearer 205 and also connected to an upper leg support via a knee joint. Such exoskeleton leg arrangements are generally known in the art and therefore will not discussed in detail.

Figures 2C, 2D, 2E:
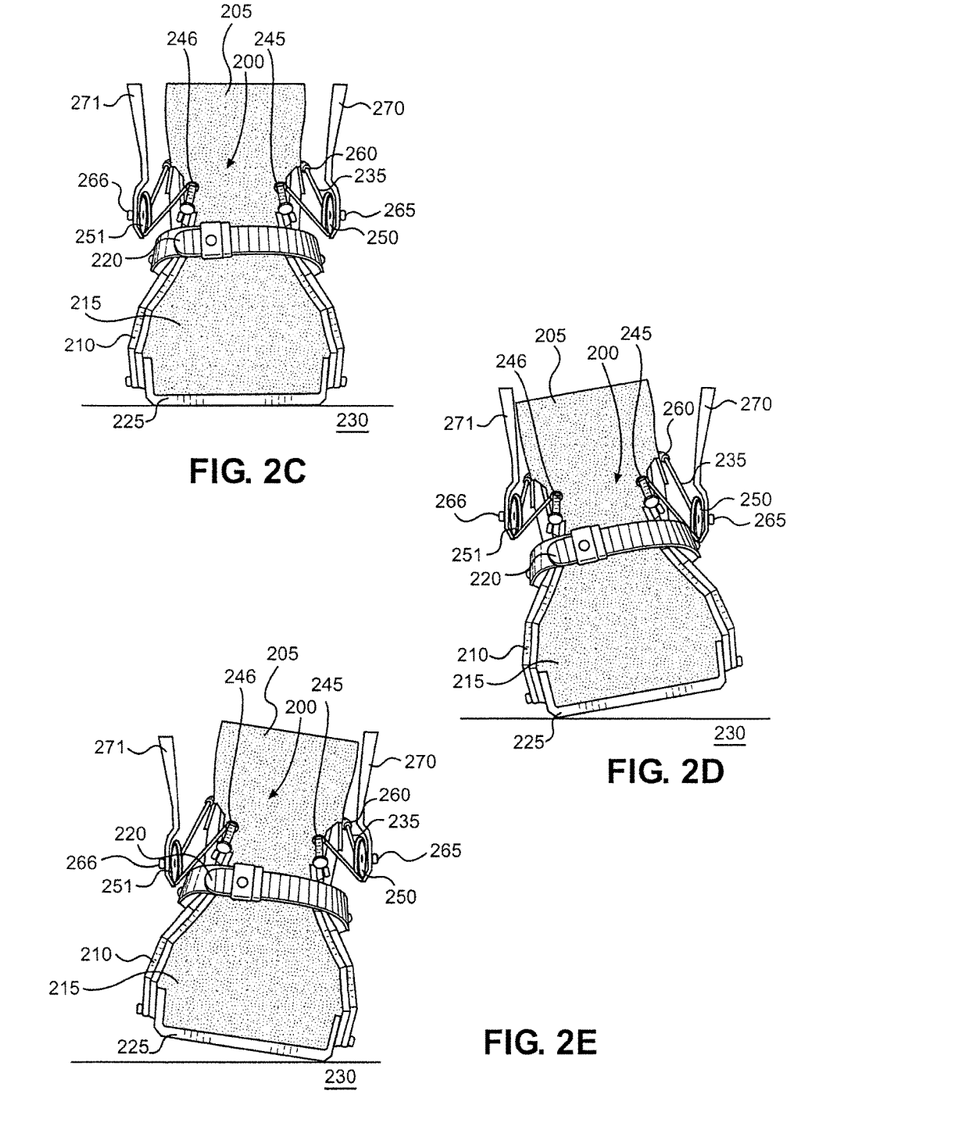
FIG. 2C is a front view of the exoskeleton ankle joint of the second embodiment with an ankle shown in a neutral position.
FIG. 2D is a front view of the exoskeleton ankle joint of the second embodiment with the ankle shown in inversion.
FIG. 2E is a front view of the exoskeleton ankle joint of the second embodiment with the ankle shown in eversion.

FIG. 2C is a front view of joint 200. As a result, the right side of joint 200 can be seen. As discussed above, tensile member 235 is directly coupled to left front support 240 at left attachment point 245. Tensile member 235 is wrapped around left pulley 250 and passes through left rear support 255 into tensile member guide 260. In addition, tensile member 235 is directly coupled to a right front support 241 at a right attachment point 246. Tensile member 235 is wrapped around a right pulley 251 and passes through a right rear support 256 into tensile member guide 260. Right pulley 251 rotates about a bearing 266, which connects right pulley 251 to a right lower leg support 271. In general, joint 200 functions in the same manner as joint 100 even though the orientations of joints 100 and 200 are reversed. That is, pulleys 115 and 116 of joint 100 are coupled to the bottom compression member (i.e., lower compression member 110), while pulleys 250 and 251 of joint 200 are coupled to the top compression member (i.e., left lower leg support 270). Accordingly, the weight borne by lower leg supports 270 and 271 is transferred through pulleys 250 and 251 into tensile member 235, with tensile member 235 transferring the weight to boot support 210 through front supports 240 and 241, rear supports 255 and 256 and tensile member guide 260. In this way, the weight borne by lower leg supports 270 and 271 is transferred to boot support 210 and then to support surface 230 through ground interaction structure 225, without the weight passing though boot 215 or the wearer's right foot.

The mechanical design of the second embodiment of the present invention improves the flexibility of the exoskeleton ankle joint, relative to current exoskeleton ankle joints, in inversion, eversion, lateral, and medial rotational motions, in addition to allowing the plantarflexion and dorsiflexion movements available in current exoskeleton ankle joints. This improved flexibility results from the ability of the rigid compression members to pivot at the interface with the flexible tensile member, as well as translate along the length of the flexible tensile member. FIGS. 2D and 2E illustrate the flexibility of joint 200 in inversion and eversion relative to a neutral ankle position, which is shown in FIG. 2C. FIGS. 2G and 2H illustrate the flexibility of joint 200 in medial and lateral rotation relative to a neutral ankle position, which is shown in FIG. 2F.

FIG. 2D is a front view of joint 200, with boot 215 shown inverting about joint 200. Since joint 200 is in inversion, a greater portion of the length of tensile member 235 is located on the left side of joint 200 (the right side of the page), tensile member 235 having translated though tensile member guide 260 during movement of boot 215 from the neutral position shown in FIG. 2C. FIG. 2E is a front view of joint 200, with boot 215 shown everting about joint 200. Since joint 200 is in eversion, a greater portion of the length of tensile member 235 is located on the right side of joint 200 (the left side of the page), tensile member 235 having translated though tensile member guide 260 during movement of boot 215 from the neutral position shown in FIG. 2C. These inversions and eversions at joint 200 can take place either with boot 215 lifted from support surface 230 or when boot 215 is in contact with a non-level or irregular support surface (not shown). In the latter case, the weight borne by lower leg supports 270 and 271 is transferred through joint 200 to boot support 210 and then to support surface 230, without the weight passing though boot 215 or the wearer's foot.

Figure 2F:
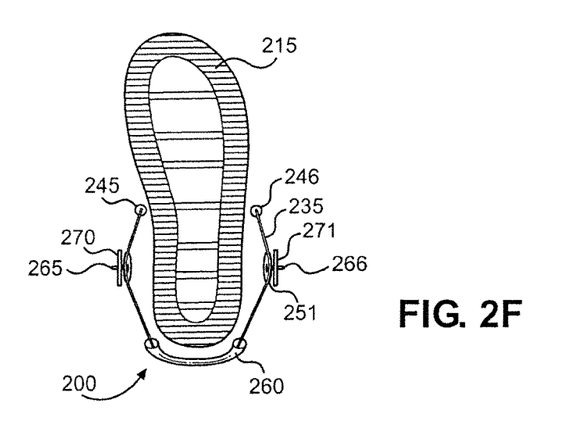
FIG. 2F is an overhead representation of the exoskeleton ankle joint of the second embodiment with the ankle and a leg shown in a neutral position.
Figure 2G:
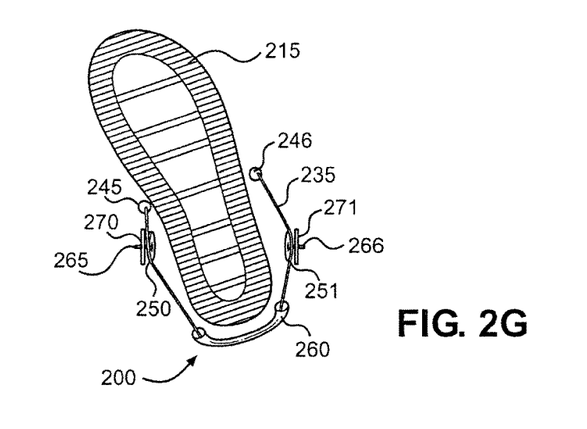
FIG. 2G is an overhead representation of the exoskeleton ankle joint of the second embodiment with the ankle and leg shown in medial rotation.
Figure 2H:
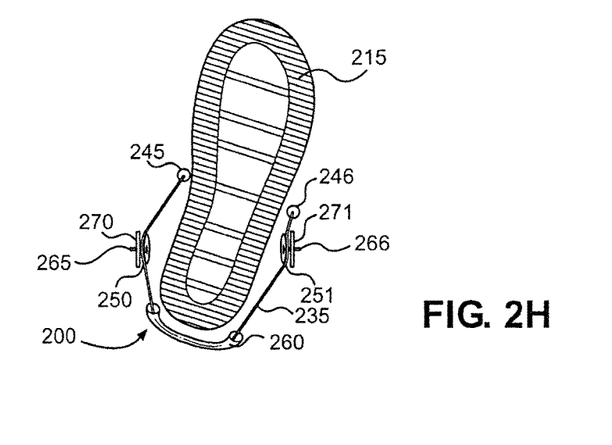
FIG. 2H is an overhead representation of the exoskeleton ankle joint of the second embodiment with the ankle and leg shown in lateral rotation.

FIG. 2F is an overhead view of joint 200, with boot 215 and joint 200 shown in a neutral position. FIG. 2G is an overhead view of joint 200, with boot 215 and joint 200 shown in medial rotation. Since joint 200 is in medial rotation, a greater portion of the length of tensile member 235 is now located between right attachment point 246 and right pulley 251, as well as between left pulley 250 and tensile member guide 260, tensile member 235 having translated through tensile member guide 260 and around pulleys 250 and 251 during movement of boot 215 from the neutral position shown in FIG. 2F. FIG. 2H is an overhead view of joint 200, with boot 215 and joint 200 shown in lateral rotation. Since joint 200 is shown in lateral rotation, a greater portion of the length of tensile member 235 is now located between left attachment point 245 and left pulley 250, as well as between right pulley 251 and tensile member guide 260, tensile member 235 having translated though tensile member guide 260 and around pulleys 250 and 251 during movement of boot 215 from the neutral position shown in FIG. 2F.

It is an inherent feature of the joint design of the first embodiment of the present invention that joint flexibility is increased when the joint is not under load, whereas the stability of the joint is increased when the joint is under load. This principle applies to an ankle joint of the second embodiment in a useful way, where a loaded ankle in stance is somewhat stabilized, and where an unloaded ankle has more freedom. This is desirable for use in a human exoskeleton device to allow for maximum flexibility in an ankle that is not in contact with the ground without resulting in an unstable ankle during stance. In some embodiments, the tensile member is inelastic, providing increased stability to the joint. In other embodiments, the tensile member, or sections thereof, has some elasticity, providing some shock absorbency to the joint. In some embodiments, the length of the tensile member can be adjusted, thereby allowing for increased flexibility in some settings and increased stability in other settings.

As an example of the second embodiment of the present invention, consider an exoskeleton and wearer walking along a smooth and level surface, such as a paved road that adjoins uneven and sloped terrain. Current exoskeleton ankles are sufficient for use on the road, but the limited ankle flexibility, particularly with regard to inversion or eversions at the ankle joint, makes walking along a slope or over irregular ground challenging and potentially dangerous. In certain situations, such as in a combat environment, walking along roads carries with it significantly increased risk of injury resulting from improvised explosive devices, mines, or small arms fire, making it very advantageous for a human exoskeleton to have the flexibility to cross uneven or sloped terrain. Through the use of the device of the second embodiment, the wearer of a human exoskeleton is able to choose whatever route is most desirable for a given situation, regardless of the uneven nature of many surfaces, including either natural terrain or terrain with complicated man-made features, as the ability of the exoskeleton ankle to invert or evert allows for better traction on these surfaces. This increased traction is due to the fact that more of the bottom of the wearer's boots is in contact with the surface across which the wearer is walking. In addition, the increased ability of the exoskeleton ankle to rotate aids in navigation over uneven surfaces by making it easier for the wearer to turn the exoskeleton around or towards certain terrain features.

FIGS. 3A-D show an exoskeleton abdominal joint 300 constructed in accordance with a third embodiment of the present invention. In general, joint 300 connects exoskeleton waist and hip structures to an exoskeleton torso structure. With initial reference to FIGS. 3A and 3B, an exoskeleton 305 is worn by wearer 205. Exoskeleton 305 includes a chest plate 310 and a back plate 315 (collectively defining a torso support), which are connected by a side plate 320 and strapping 325. Joint 300 includes a tensile member 330 connected to chest plate 310 at a left attachment point 335. Tensile member 330 wraps around left pulleys 340 and 342 and is routed into a tensile member guide 345, which is directly coupled to or formed integrally with back plate 315. Tensile member 330 also wraps around right pulleys 341 and 343 and is connected to chest plate 310 at a right attachment point 336. Pulleys 340-343 are directly coupled to a waist support 350, which is coupled to the waist of wearer 205 by a waist strap 355. Waist support 350 is rotatably coupled to an upper leg support 360 at a hip joint 365. Upper leg support 360 is coupled to a thigh of wearer 205 by a thigh brace 370 and rotatably coupled to a lower leg support 375 at a knee joint 380. Lower leg support 375 is coupled to a lower leg of wearer 205 by a lower leg brace 385. Lower leg support 375 is also coupled to a rigid boot support 390 at an ankle joint 395. Boot support 390 is in contact with support surface 230. Joint 395 is a tensegrity joint constructed in accordance with the second embodiment of the present invention.

Figure 3A:
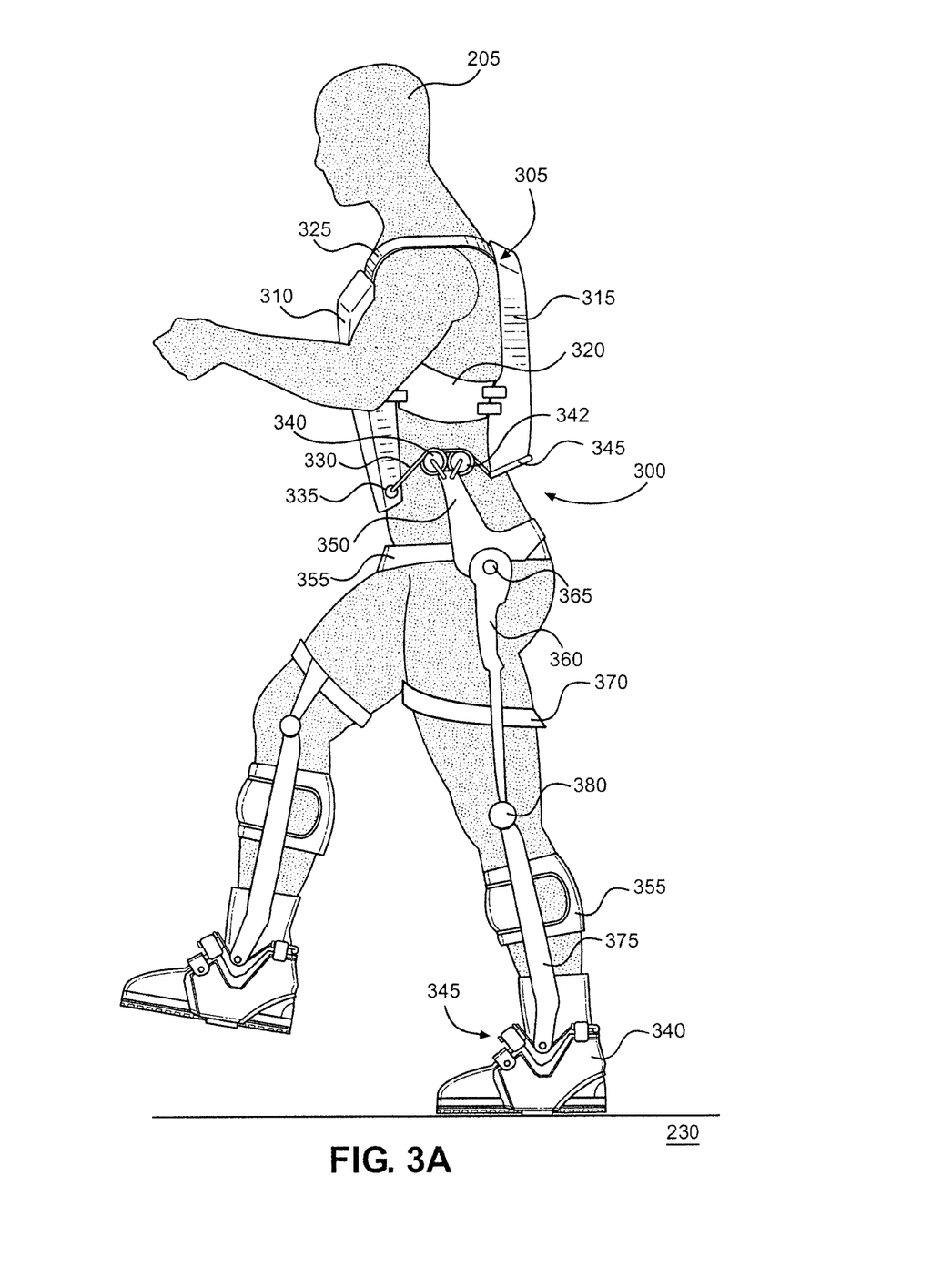
FIG. 3A is a side view of a person and exoskeleton, the exoskeleton having a torso and abdomen joint constructed in accordance with a third embodiment of the present invention.
Figure 3B:
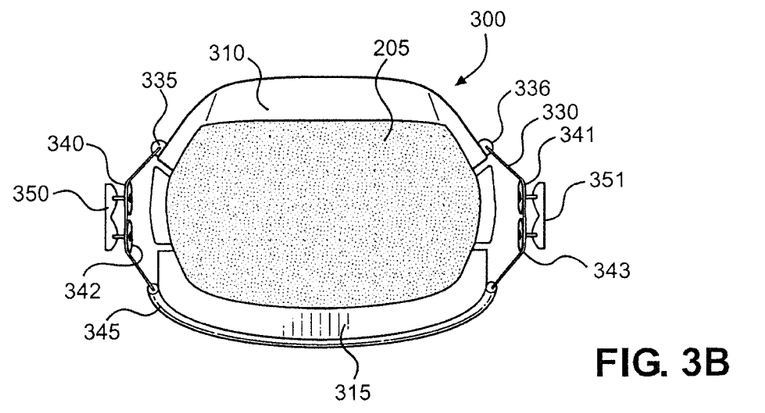
FIG. 3B is an overhead representation of the exoskeleton torso and abdomen joint of the third embodiment with a torso shown in a neutral position.

As a result of this arrangement, the weight of chest plate 310, back plate 315 and side plate 320 is transferred into tensile member 330 through attachment points 335 and 336 and tensile member guide 345. Tensile member 330 then transfers this weight to waist support 350 through pulleys 340-343 such that the weight is transferred across joint 300. From waist support 350, the weight is transferred to support surface 230 through upper leg support 360, lower leg support 375, joint 395 and boot support 390. In some embodiments, only one pulley is used on each side of joint 300. In some embodiments, the relative connectivity of tensile member 330 to chest plate 310 and back plate 315 is switched (i.e., tensile member guide 345 is coupled to chest plate 310 and attachment points 335 and 336 are located on back plate 315). In some embodiments, tensile member 330 is inelastic. In other embodiments tensile member 330, or sections thereof, has some elasticity, this elasticity granting some shock absorbency to joint 300.

In another embodiment, the device is designed so as to be easily attached and detached at joint 300, allowing separation of the torso portion of exoskeleton 305 from the rest of exoskeleton 305. In another embodiment, the length of tensile member 330 can be adjusted.

Figure 3C:
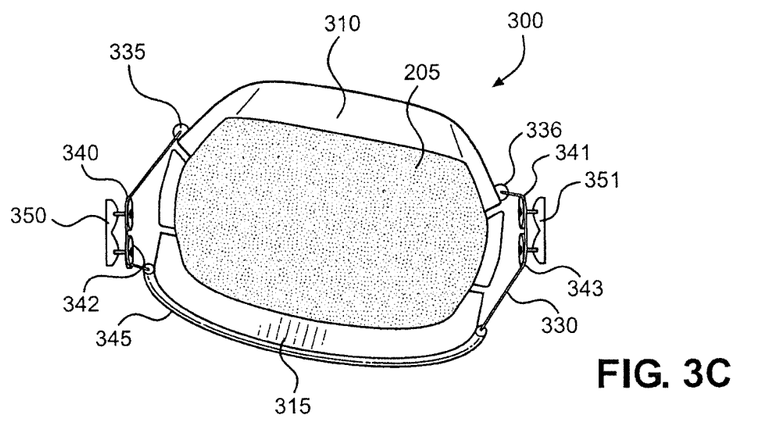
FIG. 3C is an overhead representation of the exoskeleton torso and abdomen joint of the third embodiment with the torso shown rotated to the right relative to an abdomen.
Figure 3D:
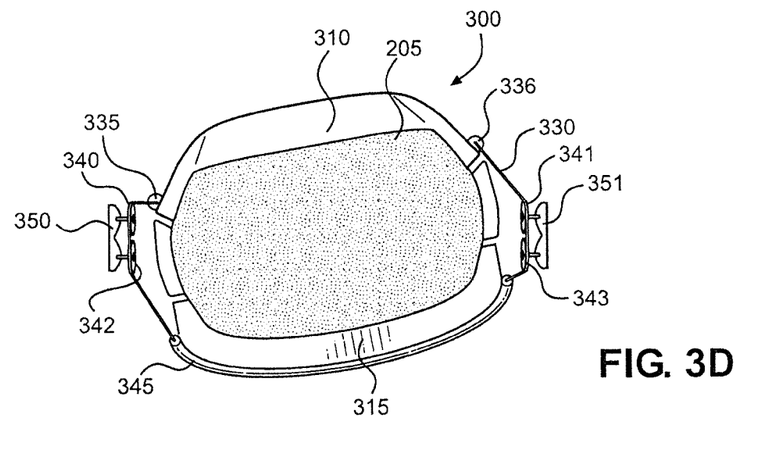
FIG. 3D is an overhead representation of the exoskeleton torso and abdomen joint of the third embodiment with the torso shown rotated to the left relative to the abdomen.

The mechanical design of the third embodiment of the present invention improves the flexibility of the exoskeleton abdominal joint, relative to current exoskeleton abdominal joints, in tilting and rotational motions, with the range of motion at this joint being similar to that of the ankle joint of the second embodiment. FIGS. 3C and 3D show abdominal joint 300 with the upper body of wearer 205 twisted relative to the lower body of wearer 205. Specifically, in FIG. 3C, the upper body of wearer 205 is twisted to the right relative to the lower body of wearer 205. As a result, chest plate 310 is twisted to the right, while waist support 350 remains in a neutral position. Also, a greater portion of the length of tensile member 330 is now located between left attachment point 335 and left pulleys 340 and 342, as well as between right pulleys 341 and 343 and tensile member guide 345, tensile member 330 having translated though tensile member guide 345 and around pulleys 340-343 during movement from the neutral position shown in FIG. 3B.

In FIG. 3D, the upper body of wearer 205 is twisted to the left relative to the lower body of wearer 205. As a result, chest plate 310 is twisted to the left, while waist support 350 remains in a neutral position. Also, a greater portion of the length of tensile member 330 is now located between right attachment point 336 and right pulleys 341 and 343, as well as between left pulleys 340 and 342 and tensile member guide 345, tensile member 330 having translated though tensile member guide 345 and around pulleys 340-343 during movement from the neutral position shown in FIG. 3B.

As an example of the third embodiment of the present invention, consider an exoskeleton being worn by a soldier in a combat environment. As the solder walks forward, with the abdominal joint in the neutral position to facilitate walking, the soldier spots a potential threat to the left. The soldier rotates his or her torso (and accordingly the exoskeleton torso) to the left in the transverse plane about the abdominal joint in order to facilitate shouldering a rifle into a firing position. Upon determination that the potential threat is not of continued interest, the soldier returns his or her torso to the neutral position to facilitate walking. Not only does the joint of the third embodiment assist in torso rotation, it does so without requiring heavy components, thereby reducing the weight of the exoskeleton and increasing the potential speed of the exoskeleton and wearer.

Figure 4:
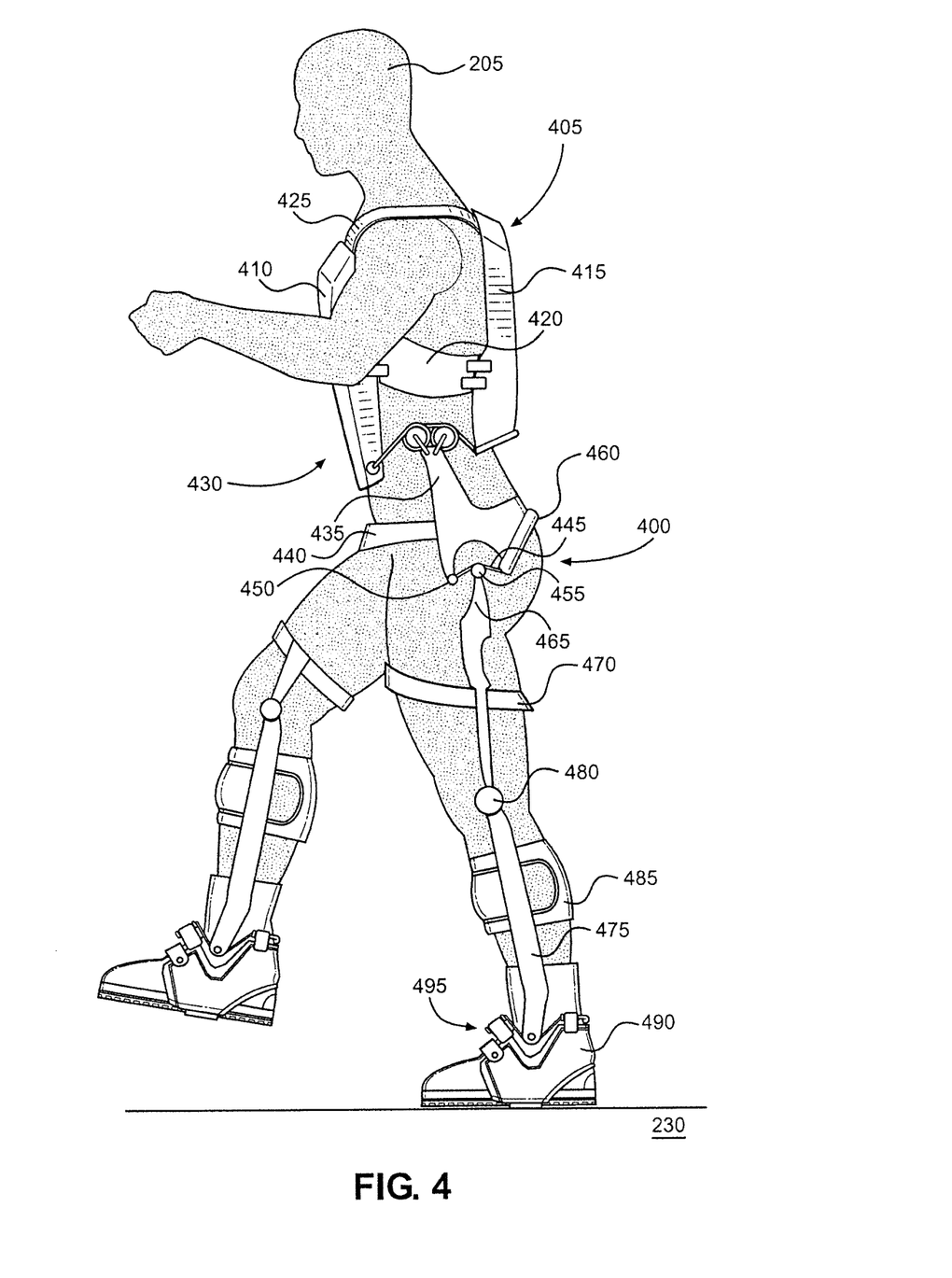
FIG. 4 is a side view of a person and exoskeleton, the exoskeleton having a hip joint constructed in accordance with a fourth embodiment of the present invention.

With reference now to FIG. 4, an exoskeleton hip joint 400 constructed in accordance with a fourth embodiment of the present invention is shown. In general, joint 400 connects an exoskeleton waist structure to an exoskeleton leg structure. More specifically, an exoskeleton 405 is worn by wearer 205. As with exoskeleton 305, exoskeleton 405 includes a chest plate 410 and a back plate 415 (collectively defining a torso support), which are connected by a side plate 420 and strapping 425. An abdominal joint 430 constructed in accordance with the third embodiment of the present invention connects chest plate 410 and back plate 415 to a waist support 435, which is coupled to the waist of wearer 205 by a waist strap 440. Joint 400 includes a tensile member 445 connected to waist support 435 at a left attachment point 450. Tensile member 445 wraps around a left pulley 455 and is routed into a tensile member guide 460, which is directly coupled to or formed integrally with waist support 435. Similar to tensile member 330 of the third embodiment, tensile member 445 also wraps around a right pulley (not shown) and is connected to waist support 435 at a right attachment point (not shown). Left pulley 455 is directly coupled to a left upper leg support 465, which is coupled to a thigh of wearer 205 by a thigh brace 470. The right pulley is directly coupled to a corresponding right upper leg support (not shown). Upper leg support 465 is rotatably coupled to a lower leg support 475 at a knee joint 480, and lower leg support 475 is coupled to a lower leg of wearer 205 by a lower leg brace 485. Lower leg support 475 is also coupled to a rigid boot support 490 at an ankle joint 495. Boot support 490 is in contact with support surface 230. Joint 495 is a tensegrity joint constructed in accordance with the second embodiment of the present invention.

As a result of this arrangement, the weight of chest plate 410, back plate 415 and side plate 420 is transferred through joint 430 to waist support 435. From waist support 435, the weight is transferred to tensile member 445 through left attachment point 450 and tensile member guide 460. Tensile member 445 then transfers the weight to upper leg support 465 through pulley 455 such that the weight is transferred across joint 400. Next, the weight is transferred to support surface 230 through lower leg support 475, joint 495 and boot support 490.

The mechanical design of the fourth embodiment of the present invention increases the flexibility of the exoskeleton hip joint in adduction and abduction movements and in lateral and medial rotational motions, in addition to allowing the extension and flexion movements available in current exoskeletons hip joints. Like the second embodiment, the device of the fourth embodiment is more stable under load and more flexible when not under load. As a result, the hip joint is somewhat stabilized during stance, while maintaining maximum flexibility when the leg with which this device is used is not in contact with the ground. In some embodiments, tensile member 445 is inelastic. In other embodiments, tensile member 445, or sections thereof, has some elasticity, this elasticity granting some shock absorbency to joint 400. In some embodiments, the length of tensile member 445 can be adjusted.

As an example of the fourth embodiment, consider an exoskeleton and wearer sitting in the front passenger seat of a vehicle. If the wearer wanted to open the door of the vehicle and exit the vehicle using a motion similar to that used by a person not wearing an exoskeleton, it would require a number of hip motions, including adduction and abduction of both legs as well as lateral rotation at the hip and other movements. This combination of movements would be very difficult for current exoskeletons with limited hip flexibility. However, with an exoskeleton constructed in accordance with the fourth embodiment, the wearer is able to use the increased hip flexibility, particularly when the hips are not under load as in a seated position, in order to dismount and exit the vehicle.

In view of the above description, it should be recognized that tensegrity joints can be implemented in a variety of different locations within an exoskeleton. As a further example, a segmented neck and helmet of an exoskeleton can make use of a series of tensegrity joints, constructed in accordance with the first embodiment, thereby allowing the neck to bear the weight of the helmet and neck armor and transfer this weight around the body of the wearer into a support surface upon which the exoskeleton is standing. In another example, a segmented, p-linked spine, neck, and helmet of an exoskeleton can make use of a series of tensegrity joints, constructed in accordance with the first embodiment, thereby allowing the spine to bear the weight of the helmet, neck armor, chest armor and back armor and transfer this weight around the body of the wearer into a surface upon which the exoskeleton is standing. In yet another example, a segmented series of shoulder, wrist, and arm joints of an exoskeleton can make use of a series of tensegrity joints, constructed in accordance with the first embodiment, thereby allowing highly flexible armored arms to be affixed to an exoskeleton.

In general, the types of tensegrity joints described in connection with the present invention will perform better in the context of an exoskeleton than in the context of a robot because the wearer of the exoskeleton can provide some constraint and stability to the joint though the balance and control of the wearer.

In all embodiments of the present invention, the tensegrity joint can be configured so as to maximize flexibility about the joint. In all embodiments, the tensegrity joint can be configured so as to minimize exoskeleton weight. In all embodiments, the tensegrity joint can be configured so as to maximize the weight bearing capacity of the exoskeleton. In all embodiments, the tensile member can be inelastic. In all embodiments, the tensile member can have some elasticity. In all embodiments, tensegrity joint can be covered in some way so as to prevent vegetation, clothing or other materials from becoming caught in or interfering with the function of the joint. In all embodiments, the supports connecting the tensile member to the exoskeleton can be rigid, incompressible or inflexible. In all embodiments, the supports connecting the tensile member to the exoskeleton can be somewhat compressible or flexible. In all embodiments, the tensile member can be compressible. In all embodiments, the length and or tension upon the tensile member can be adjustable. In all embodiments, the tensile member can be rapidly detachable or replaceable.

Based on the above, it should be readily apparent that the present invention provides improved flexibility in weight-bearing exoskeleton joints. Although described with reference to preferred embodiments, it should be readily understood that various changes or modifications could be made to the invention without departing from the spirit thereof. In general, the invention is only intended to be limited by the scope of the following claims.

The invention claimed is:
1. An exoskeleton comprising:
a first compression member configured to be coupled to a wearer of the exoskeleton;
a second compression member configured to be coupled to the wearer;
a tensegrity joint connecting the first compression member to the second compression member, the joint including a tensile member having a first end and a second end, wherein the first end is coupled to the first compression member on a first side of the joint, and the second end is coupled to the first compression member on a second side of the joint opposite the first side, and wherein:
  each of the first and second ends is directly coupled to the first compression member; or
  the first end is directly coupled to a first support, the second end is directly coupled to a second support and each of the first and second supports is directly coupled to the first compression member.

2. The exoskeleton of claim 1, wherein the joint further includes a tensile member guide through which the tensile member passes.

3. The exoskeleton of claim 1, wherein:
  the joint is an exoskeleton ankle joint;
  one of the first and second compression members is a lower leg support; and
  the other of the first and second compression members is a boot support.

4. The exoskeleton of claim 1, wherein:
  the joint is an exoskeleton abdominal joint;
  one of the first and second compression members is a torso support; and
  the other of the first and second compression members is a waist support.

5. The exoskeleton of claim 1, wherein:
  the joint is an exoskeleton hip joint;
  one of the first and second compression members is a waist support; and
  the other of the first and second compression members is an upper leg support.

6. The exoskeleton of claim 1, wherein the joint constitutes a first tensegrity joint, the exoskeleton further comprising:
  a third compression member configured to be coupled to the wearer;
  a second tensegrity joint connecting the second compression member to the third compression member, the second tensegrity joint including a tensile member having a first end and a second end, wherein the first end is coupled to the second compression member on a first side of the second tensegrity joint, and the second end is coupled to the second compression member on a second side of the second tensegrity joint opposite the first side.

7. The exoskeleton of claim 1, wherein the exoskeleton is configured such that weight borne by one of the first and second compression members is transferred to the other of the first and second compression members through the tensile member.

8. An exoskeleton comprising:
  a first compression member configured to be coupled to a wearer of the exoskeleton;
  a second compression member configured to be coupled to the wearer;
  a tensegrity joint connecting the first compression member to the second compression member, the joint including a tensile member having a first end and a second end, wherein the first end is coupled to the first compression member on a first side of the joint, the second end is coupled to the first compression member on a second side of the joint opposite the first side, the joint further includes a first pulley on the first side of the joint and a second pulley on the second side of the joint, and the tensile member is wrapped around each of the first and second pulleys.

9. The exoskeleton of claim 8, wherein each of the first and second pulleys is connected to the second compression member.

10. The exoskeleton of claim 9, wherein:
  each of the first and second pulleys is directly coupled to the second compression member; or
  the first pulley is directly coupled to a first support, the second pulley is directly coupled to a second support and each of the first and second supports is directly coupled to the second compression member.

11. A method of increasing flexibility of a joint of an exoskeleton including a first compression member configured to be coupled to a wearer of the exoskeleton, a second compression member configured to be coupled to the wearer and a tensegrity joint connecting the first compression member to the second compression member, the method comprising:
  configuring the joint as a tensegrity joint by coupling a first end of a tensile member to the first compression member on a first side of the joint and coupling a second end of the tensile member to the first compression member on a second side of the joint opposite the first side, and further comprising:
  directly coupling each of the first and second ends to the first compression member; or
  directly coupling the first end to a first support and directly coupling the second end to a second support, wherein each of the first and second supports is directly coupled to the first compression member.

12. The method of claim 11, further comprising passing the tensile member through a tensile member guide.

13. The method of claim 11, wherein the joint is an exoskeleton ankle joint, one of the first and second compression members is a lower leg support and the other of the first and second compression members is a boot support, the method further comprising:
  coupling the lower leg support to a lower leg of the wearer; and
  coupling the boot support to a boot worn by the wearer.

14. The method of claim 11, wherein the joint is an exoskeleton abdominal joint, one of the first and second compression members is a torso support and the other of the first and second compression members is a waist support, the method further comprising:
  coupling the torso support to a torso of the wearer; and
  coupling the waist support to a waist of the wearer.

15. The method of claim 11, wherein the joint is an exoskeleton hip joint, one of the first and second compression members is a waist support and the other of the first and second compression members is an upper leg support, the method further comprising:
  coupling the waist support to a waist of the wearer; and
  coupling the upper leg support to an upper leg of the wearer.

16. The method of claim 11, wherein the joint constitutes a first joint, and the exoskeleton further includes a third compression member configured to be coupled to the wearer and a second joint connecting the second compression member to the third compression member, the method further comprising:
  configuring the second joint as a tensegrity joint by coupling a first end of a tensile member to the second compression member on a first side of the second joint and coupling a second end of the tensile member to the second compression member on a second side of the second joint opposite the first side.

17. A method of increasing flexibility of a joint of an exoskeleton including a first compression member configured to be coupled to a wearer of the exoskeleton, a second compression member configured to be coupled to the wearer and a tensegrity joint connecting the first compression member to the second compression member, the method comprising:
- configuring the joint as a tensegrity joint by coupling a first end of a tensile member to the first compression member on a first side of the joint and coupling a second end of the tensile member to the first compression member on a second side of the joint opposite the first side, wherein the joint further includes a first pulley on the first side of the joint and a second pulley on the second side of the joint; and
- wrapping the tensile member around each of the first and second pulleys.

18. The method of claim 17, further comprising connecting each of the first and second pulleys to the second compression member.

19. The method of claim 18, further comprising:
- directly coupling each of the first and second pulleys to the second compression member; or
- directly coupling the first pulley to a first support and directly coupling the second pulley to a second support, wherein each of the first and second supports is directly coupled to the second compression member.

* * * * *